United States Patent [19]
Muller et al.

[11] Patent Number: 5,993,441
[45] Date of Patent: Nov. 30, 1999

[54] CONTROL OF PHOTOREFRACTIVE KERATECTOMY

[75] Inventors: David F. Muller, Boston; Alex C. Sacharoff; Peter J. Klopotek, both of Framingham, all of Mass.

[73] Assignee: Summit Technology, Inc., Waltham, Mass.

[21] Appl. No.: 08/695,673

[22] Filed: Aug. 8, 1996

Related U.S. Application Data

[63] Continuation of application No. 08/580,042, Dec. 20, 1995, abandoned, which is a continuation of application No. 08/224,837, Apr. 8, 1994, abandoned.

[51] Int. Cl.$^6$ .................................................. A61N 5/06
[52] U.S. Cl. ................................... 606/10; 606/2; 606/5; 606/13
[58] Field of Search ............................... 606/3–6, 10–18

[56] References Cited

U.S. PATENT DOCUMENTS

| | | |
|---|---|---|
| 4,718,418 | 1/1988 | L'Esperance, Jr. .......................... 606/3 |
| 4,733,944 | 3/1988 | Fahlen et al. . |
| 4,856,513 | 8/1989 | Muller . |
| 4,941,093 | 7/1990 | Marshall et al. ............................. 606/5 |
| 4,994,058 | 2/1991 | Raven et al. . |
| 5,019,074 | 5/1991 | Muller . |
| 5,091,626 | 2/1992 | Lewis et al. . |
| 5,163,934 | 11/1992 | Munnerlyn . |

FOREIGN PATENT DOCUMENTS

| | | |
|---|---|---|
| 0 080 597 B1 | 6/1983 | European Pat. Off. . |
| 2 180 363 | 3/1987 | United Kingdom . |

OTHER PUBLICATIONS

Bor, Z. et al. (1993) "Physical problems of excimer laser cornea ablation" *Optical Engineering* 32:2481–2486.

Bruno, R.J. and K.C. Liu (1987) "Laserbeam Shaping for Maximum Uniformity and Minimum Loss" *Lasers & Applications* Apr. 1987:91–94.

Deng, X. et al. (1986) "Uniform illumination of large targets using a lens array" *Applied Optics* 25(3):377–381.

Grojean, R.E. et al. (1980) "Production of flat top beam profiles for high energy lasers" *Rev. Sci. Instrum.* 51(3):375–376.

Han, C.–Y. et al. (1983) "Reshaping collimated laser beams with Gaussian profile to uniform profiles" *Applied Optics* 22(22):3644–3647.

Horton, T.E. and J.H. McDermit (1972) "Design of a Specular Aspheric Surface to Uniformly Radiate a Flat Surface using a Nonuniform Collimated Radiation Source" *J. Heat Transfer* Nov. 1972:453–458.

(List continued on next page.)

*Primary Examiner*—David M. Shay
*Attorney, Agent, or Firm*—Thomas J. Engellenner; Lahive & Cockfield, LLP

[57] ABSTRACT

A method and system are described for performing photorefractive keratectomy procedure employing pulses of photoablative radiation to selectively ablate corneal tissue of a patient's eye in an ablation zone on the anterior corneal surface to produce a desired refractive correction in the corneal tissue. The method and system employ control of the effect of ocular fluid at the corneal surface so as to reduce the disturbance of such fluid on the desired ablation process while maintaining hydration of the corneal tissue. Controlling the average repetition rate of the radiation pulses applied to the corneal surface so as to reduce intrapulse fluid accumulation at the corneal surface without dehydrating the corneal tissue, selecting an increased fluence level of the pulse applied to the corneal surface to reduce the effect of fluid accumulation at the corneal surface, and applying evaporative energy to the site of incidence of a pulse of an ablative beam prior to incidence of said pulse at said site are shown as ways to effect this control. Application of the new method and system to wide area ablation techniques and to scanning techniques are described Reduction of irregularities when ablating large areas, e.g., grater than 5.5 cm is made possible in either case.

6 Claims, 11 Drawing Sheets

OTHER PUBLICATIONS

Iwasaki, K. et al. (1983) "Flattening Laserbeam Intensity Distribution" *Lasers & Applications* Apr. 1993:76,78.

Krueger, R.R. et al. (1993) "Corneal Surface Morphology Following Excimer Laser Ablation With Humidified Gases" *Arch. Ophthalmol.* 111:1131–1137.

Lacombat, M. et al. (1980) "Laser Projection Printing" *Solid State Technology* Aug. 1980:115–121.

Morrill, K. (1993) "Theories presented on PRK's 'central islands'" *Ocular Surgery News* Sep. 15, 1993:26–27.

Ozaki, Y. and K. Takamoto (1989) "Cylindrical fly's eye lens for intensity redistribution of an excimer laser beam" *Applied Optics* 28(1):106–110.

Piebenga, L.W. et al. (1993) "Excimer Photorefractive Keratectomy for Myopia" *Ophthalmology* 100:1335–1345.

Rhodes, P.W. and D.L. Shealy (1980) "Refractive optical systems for irradiance redistribution of collimated radiation: their design and analysis" *Applied Optics* 19(20):3545–3553.

Tabat, M. et al. (1992) "Profile characteristics of excimer laser micromachined features" *SPIE: Excimer Lasers* 1835:144–157.

Wright, M. (1993) "Corneal Islands Minimized by Latest Refinements" *Ophthalmology Times* Sep. 15, 1993.

Emphasis™ Erodible Flask Brochure (May 1993).

CONTROL OF PHOTOREFRACTIVE KERATECTOMY

This application is a continuation of application Ser. No. 08/580,042, filed Dec. 20, 1995, now abandoned which is a continuation of application Ser. No. 08/224,837 filed Apr. 8, 1994, Entitled: CONTROL OF PHOTOREFRACTIVE KERATECTOMY, now abandoned.

BACKGROUND

This invention relates to improvements in photorefractive keratectomy (PRK).

In PRK, corneal tissue is removed in a controlled fashion to shape the surface of the cornea of a patient's eye to treat, e.g., myopia, hyperopia, presbyopia or astigmatism The cornea comprises transparent avascular tissue that forms the anterior portion of the eye. The cornea functions as both a protective membrane and a "window" through which light passes as it proceeds to the retina. The transparency of the cornea is due to its uniform structure, avascularity, and deturgescence, which is the state of relative hydration of the corneal tissue.

A major proportion of the refractive power of the eye is determined by the curvature of the anterior surface of the cornea, so that changing the shape of the cornea offers a way to significantly reduce a refractive problem in the eye.

Various techniques have been proposed for shaping the cornea of a patient's eye. Some techniques include removing the epithelium, and then shaping the underlying Bowman's and stroma layers. In PRK, photoablation is employed using e.g., ultraviolet radiation from an excimer laser, e.g., at 193 nm wavelength, or infrared laser radiation that has a wavelength in the range of about 2.9 to 3.2 $\mu$m.

In one technique, described in Marshall et al., U.S. Pat. No. 4,941,093 (assigned to Summit Technology Inc.), the shape and size of the area of the corneal surface which is irradiated by laser radiation is selected and controlled so that some areas of the corneal surface become more eroded than others and a desired corneal shape is achieved.

Another technique, described in Muller, U.S. Pat. No. 4,856,513 (assigned to Summit Technology Inc.), uses a laser and an erodible mask. The mask, with a predefined profile of resistance to erosion by laser radiation, is disposed between the laser and the corneal surface. A portion of the laser radiation is absorbed by the mask, while another portion is transmitted to the corneal surface in accordance with the mask profile, thereby enabling the selective photoablation of the corneal surface into a desired shape.

There are circumstances in which it is desired to accomplish the PRK treatment with the ablated zone larger than 5 mm in diameter. With such zones, under usual operating conditions it has been observed that the final surface achieved by the ablation process differs from the expected shape. Surface irregularity and significant refractive error have been observed post-operatively in the corneal topographies of some patients treated for PRK. These irregularities may lead to visual disturbances such as diplopia, blurred vision, and loss of Best Corrected Visual Acuity (i.e., the vision obtained with the best possible lens correction).

The PRK procedure has achieved a clinically accepted level. However the possibility of achieving even better results with larger ablation zones has been somewhat elusive. The present invention provides a new insight into conditions that can occur in PRK and provides techniques that address these conditions to enable enhanced predictability, stability, and safety of the procedure to be achieved.

SUMMARY OF THE INVENTION

In performing a photorefractive keratectomy procedure employing pulses of photoablative radiation to selectively ablate corneal tissue of a patient's eye to produce a desired refractive correction in the corneal tissue, particularly when ablating areas larger than about 5.5 mm in diameter, we have realized that improved results can be achieved by controlling the effect of ocular fluid at the corneal surface so as to reduce the disturbance of this fluid on the ablation process while maintaining hydration of the tissue. The ocular fluid to which we refer is the physiological fluid produced naturally by the eye, which contains various proteins and solutes, and which tends to accumulate in regions subjected to photoablation. As the ablation proceeds, solid residues of the preceding ablative process also enter the fluid. The reference to the fluid being "at the corneal surface" refers to liquid on the surface and fluid present among the initial molecules that form the surface structure. By "controlling", we refer to systematic selection or adjustment of parameters of the treatment conditions in a way that takes into account the detrimental effect accumulated ocular fluid can have upon the result of the procedure relative to the correction that is desired, and the need not to dehydrate the remaining corneal tissue.

In addition to recognizing the importance of this controlling step, we have also conceived various approaches for accomplishing the step, some of which can be accomplished by simple adjustment or selection of parameters without affecting the complexity of the procedure or its cost.

In the case of wide-area ablation, in which a pulsed beam of ablative energy of variable controlled diameter is centered on the eye, it is often desired to maintain the fluence of the beam constant from pulse to pulse. We have realized that selection of the repetition rate of the optical pulse may be employed for controlling the ocular fluid effect. By employing a rate sufficiently high, in excess of 10 Hz, intrapulse fluid accumulation can be reduced at the surface to be ablated such that the aggregate disturbing effect does not result in a dioptic variation greater than a prescribed amount, for instance ¼ Diopter. Preferably the effective pulse rate is selected in the range between about 12 to 100 Hz, depending upon other parameters being employed.

In other wide-area ablation systems, the fluence of the pulses may also be selected for the purpose of controlling the effect of intrapulse fluid accumulation without dehydration of the corneal tissue. We have realized that selecting higher beam fluence levels, within a practical operating range, reduces the sensitivity of each beam pulse to intrapulse fluid accumulation. Here, advantage is taken of a saturation trend, i.e., the increase of the amount of material ablated, as the fluence increases, occurs at a rate that has a decreasing value.

In other systems, the repetition rate and fluence levels employed can both be selected based on their effect in respect of the ocular fluid problem. In sophisticated systems employing control by a computer program the values of these parameters may be varied on a case-by-case basis for controlling the effect of ocular fluid accumulation, while avoiding corneal tissue dehydration.

We have also realized that the sensitivity of the ablative process to the effects of ocular fluid accumulation is dependent upon the depth of the tissue being removed. This dependency can be understood from the following considerations. Refractive error of a procedure is typically desired to be held within a prescribed absolute tolerance, or "precision" such as ¼ Diopter. On the other hand, the disturbance caused by a given value of intrapulse accumulation of ocular fluid is cumulative, increasing for a given site with the number of pulses that are incident on the site. Furthermore, we have observed that the rate of accumulation of ocular fluid at a site increases with the depth of tissue removed. Likewise the amount of ablative residue in the fluid may increase with the depth of tissue removed. It is realized that if more ocular fluid or fluid with higher, absorptive values exists in some areas than in other areas in the ablation zone, non-uniform ablation will occur with pulses that overlap those areas. Thus the sensitivity of the ablative process to the ocular fluid problem is realized to be dependent upon the depth of tissue removal.

We have further realized it is significant that the depth of tissue removed, for a given Diopter correction, varies as a power function with the diameter of the ablation zone. The degree of disturbance of the ablation attributable to accumulated ocular fluid and the degree of required control on the effects of ocular fluid likewise are found in general to be related to a power function of the diameter of the ablation zone.

According to the invention, based on observations conducted employing beam pulses of 180 mJ cm$^{-2}$ of excimer laser pulses of 193 nm wavelength, the method and system for applying beam pulses of photoablative radiation are preferably selected so that at any given site of incidence of the beam pulses in the ablation zone, the average rate (Rep Rate, expressed in Hz) at which the beam pulses are provided, the effective average fluence (F, expressed in mJ cm$^{-2}$) of the beam pulses, and the average diameter ($\phi$, expressed in mm) of the ablation zone, have the general relationship:

$$\text{Rep Rate} \geq C \times \phi^2 / \ln(F),$$

where C is between 15 and 20.

Also because the depth of tissue varies with the Diopter value of the correction to be effected in the patient's cornea, for improved control, the system parameters can be selected to take this factor into account as well. Because it is desirable that the precision of the correction be maintained at an absolute value over the range of dioptric corrections, e.g., within ¼ Diopter, and because small localized variations in tissue depth may have a large effect upon the local refractive value, we have realized that the size of the correction in Diopter has greater than a linear effect on the degree of control needed in respect of the ocular fluid problem According to this realization, the invention also features a method and system in which the beam pulses are selected so that, at any given site of incidence of the beam pulses in the ablation zone, the average rate (Rep Rate, expressed in Hz) at which the beam pulses are provided, the effective average fluence (F, expressed in mJ cm$^{-2}$) of the beam pulses, the average diameter ($\phi$, expressed in mm) of the ablation zone, and the dioptric power (D, expressed in Diopter) at the location of maximum correction to be effected in the patient's cornea, maintain the general relationship:

$$(\phi^2 \times D^2)/(\ln(F) \times \text{Rep Rate}) \leq C',$$

where C' is about 15. This is based on observations made employing beam pulses of 180 mJ cm$^{-2}$ of excimer pulses of 193 nm wavelength, at a 6 mm diameter ablation zone, for a 5 Diopter correction at 20 Hz pulse rate.

Other techniques to control the effects of accumulating ocular fluid can be used in conjunction with the technique just described or can constitute effective control by themselves.

An evaporative effect provided uniformly can be employed to remove intrapulse accumulation of ocular fluid.

In one case, the invention features a double pulse system Immediately preceding the main pulse at ablating energy level (e.g. fluence between about 100 to 250 mJ cm$^{-2}$ in the case of pulses of 193 nm wavelength in a wide area ablation system), a precursor evaporative pulse of the same wavelength of carefully controlled energy is introduced at fluence below the ablative threshold, e.g., of 50 mJ cm$^{-2}$. The effect of the precursor pulse is to produce evaporation of accumulated ocular fluid. In order to obtain evaporation without dehydrating the corneal tissue, the parameters of the precursor beam are selected to limit the depth of the energy deposition.

In another case, a separate source of irradiation is employed which may operate continuously, intermittently, or in pulses at desired times. In one preferred embodiment, a $CO_2$ laser is employed to produce radiation at a wavelength that is highly absorbed by water. The stream of pulses of evaporative energy may advantageously be coordinated to avoid overlap of the incident pulses of evaporative and ablative wavelengths and to optimize the state of reduction of fluid accumulation without tissue dehydration at the time of incidence of the ablative pulse upon a given site.

According to another aspect of the invention, the ambient humidity at the locus of the eye is maintained at a well controlled level below saturation during the procedure to accelerate evaporation of ocular fluid that tends to accumulate This may include maintaining the room at low humidity or special provisions localized to the region of the eye, such as a gentle, general distribution of gas, at appropriate humidity to cause evaporation of accumulated ocular fluid, via a series of outlets uniformly distributed about the eye.

According to another aspect of the invention, controlling the effect that can be caused by the accumulation of ocular fluid involves reducing the tendency of the body to present such fluid at the ablative site. This can be effected by systemic or local administration of a drug that is effective to retard the fluid accumulation. Such treatment may be supplemented with control of the general thermal condition of the eye, as by cooling prior to treatment, in manner that retards flow of the ocular fluid to the ablation site.

It will be understood that the degree of control to be employed with respect to any parameter during wide area ablation for controlling the effect of ocular fluid is not to be determined in isolation, but rather out of consideration of the values of other parameters that are employed. Suffice it to say that effective wide area ablation, with ablating zones in excess of about 5.5 mm, up to about 10 mm, and in particular including the range of 6.0 mm to 8.0 mm, can be performed following the present teachings. Specifically, the present invention contributes to solving the problem of "islands" of excess tissue that have been observed as a result of operation of some ablative systems.

In certain broader aspects, the invention equally is relevant to scanning ablative systems in which the ablative beam is narrow in one or both dimensions relative to the dimension of the ablative zone, or is smaller in area than the ablation zone, and in which such beam is displaced laterally from pulse to pulse. In such systems, the intrapulse accumulation of ocular fluid relates to the period between which pulses are incident at the same point, which is typically at a much lower rate than the pulse rate of the originating laser, due to the distribution of the pulses between many different points in the ablative zone.

The considerations above apply with even greater force in respect of such scanning systems, while the nature of such systems permit control of additional parameters.

According to the invention, in such systems higher fluence levels can be selected because the opportunity for thermal build up can be reduced by judicious distribution of the pulses. Also, because of the smaller beam size, it is feasible to operate at lower controlled fluence levels. The range of practical fluence levels for scanning-type systems lies between about 80 and 500 mJ cm$^{-2}$. Likewise the repetition rate of the laser itself may be very high when scanning techniques are employed, while the local effective pulse rate of any site of incidence of the beam may be maintained over a wide range depending upon the selected fluence, but still must be sufficiently frequent, e.g., above 10 Hz, to control the effect of the ocular fluid.

It will be understood that scanning systems enable further degrees of freedom in operation and provide abilities to more readily control the effect of the ocular fluid than are provided by control of the average repetition rate and average fluence of the beam. In a scanning system, one can easily change the size of the spot. Changing the size of the spot while keeping the same total energy in the beam is an easy way to change the fluence from pulse to pulse in a very dramatic way. The repetition rate with which the system fires the pulses can likewise be very different than the repetition rate for a wide area ablation system, and can be varied. Furthermore, a given site in the ablation zone in a scanning system can be revisited by the pulses of the laser on a selected basis. Each of these variables may be implemented according to an appropriate algorithm which addresses the issues of controlling the ocular fluid. For example, according to the invention an algorithm is provided which starts to cut deeper areas, and re-visits the places which are to be deeply ablated more frequently than the places which are to be shallow-ablated The shallow-ablated regions can tolerate lower repetition rate and a resultant greater disturbance by ocular fluid per pulse, because of a lesser aggregative effect on the dioptric error. Thus the scanning system provides further degrees of freedom to employ algorithmic control by revisiting places of deeper removal with higher frequency. Such a system automatically compensates and thus distinguishes other algorithms that can be used to treat essentially the entire area over the duration of the procedure.

In certain further respects, scanning systems have a greater need to comply to the principles established above. Because the ablation occurs in a distribution of small spots or lines there is the additional possibility of lateral transport of material under the dynamic conditions of scanning and a more detrimental effect can occur if ocular fluid is permitted to accumulate. In the case of certain scanning systems, to avoid this effect, the inventors conceive it to be advantageous for each successive firing of the laser to be directed to a relatively distant, virgin place at which any accumulated fluid has not been recently dynamically disturbed by the previous firing.

These illustrate just some of the greater possibilities which scanning systems offer for controlling the effects of ocular fluid at the corneal surface.

While the physiology of the eye and its mechanisms are not fully understood at a detailed level, certain observations that lead to further insight into the present invention can be mentioned.

Ocular fluid present in the native cornea that is responsible for maintaining proper hydration of the eye may appear on the surface of the cornea within the boundaries of the treatment zone. Though this fluid is water-based, it contains substantial quantities of proteins and various solutes necessary for proper corneal function. As the corneal lamellae are ablated, ocular fluid may flow out of the stroma and tend to accumulate non-uniformly on the exposed ablated surface. During the course of the ablation treatment, the concentration in the ocular fluid of solid residues of the preceding ablative action can increase. The possibility of redeposit on the corneal surface of fluid cast into space by the ablation process is also possible. Although pure water may have little effect on the ablative beam, the biomaterial present in the fluid can have strong absorption characteristics for the photoablating laser energy used in PRK, and the absorptive character of the fluid can increase as the concentration of ablative residue increases.

It is realized that accumulated ocular fluid, particularly if it covers the tissue to be ablated, can cause the incoming photoablating laser energy to be partially absorbed before reaching the underlying stromal tissue, thereby reducing the fluence available to ablate the corneal tissue and disturbing the rate of ablation. On the other hand, if the stromal tissue is not so completely wetted by the ocular fluid, the ablation can proceed in a manner much less affected by the ocular fluid.

Non-uniform accumulations of ocular fluid over the surface being ablated are therefore believed to be detrimental to the photo-ablative process. The step of controlling the effects of accumulated ocular fluid without dehydrating the tissue solves this problem and enables use of ablative zones larger than 5 cm with improved effect.

Other features and advantages of the invention will become apparent from the following description and from the claims.

DESCRIPTION OF THE PREFERRED EMBODIMENT

Figure 1:
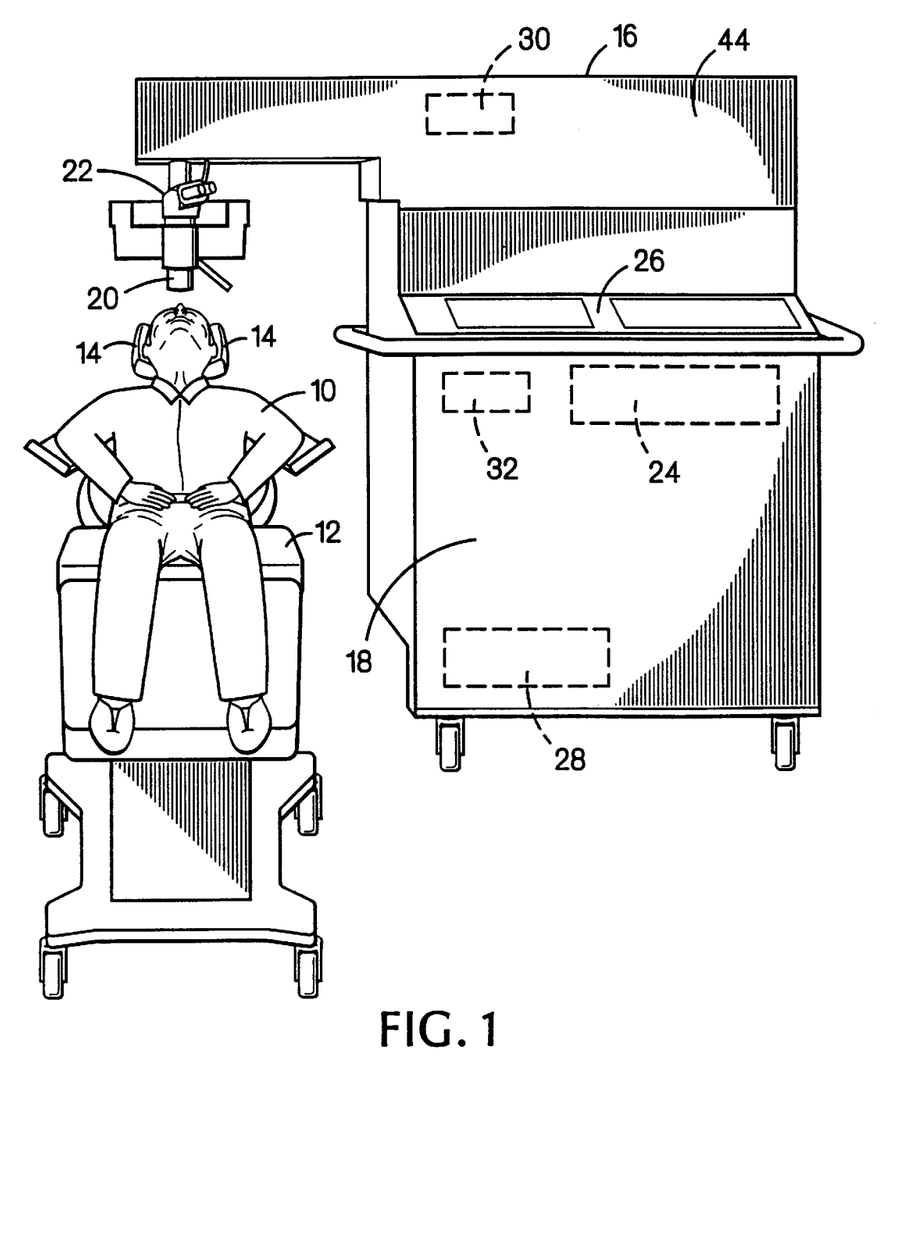
FIG. 1 is a side elevational view of a patient undergoing photoablative shaping of corneal tissue.

Referring to FIG. 1, a patient 10, lying on an operating bed 12 with his head restrained between two side supports 14, is shown undergoing photoablative shaping of the cornea in a PRK procedure in accordance with the invention.

An optical support assembly 16 supports beam delivery optics that transmit photoablative radiation from, e.g., a laser source inside housing 18 to beam delivery optics 20. During the cornea shaping procedure, the patient's eye may be observed using a surgical microscope 22.

Figure 1A:
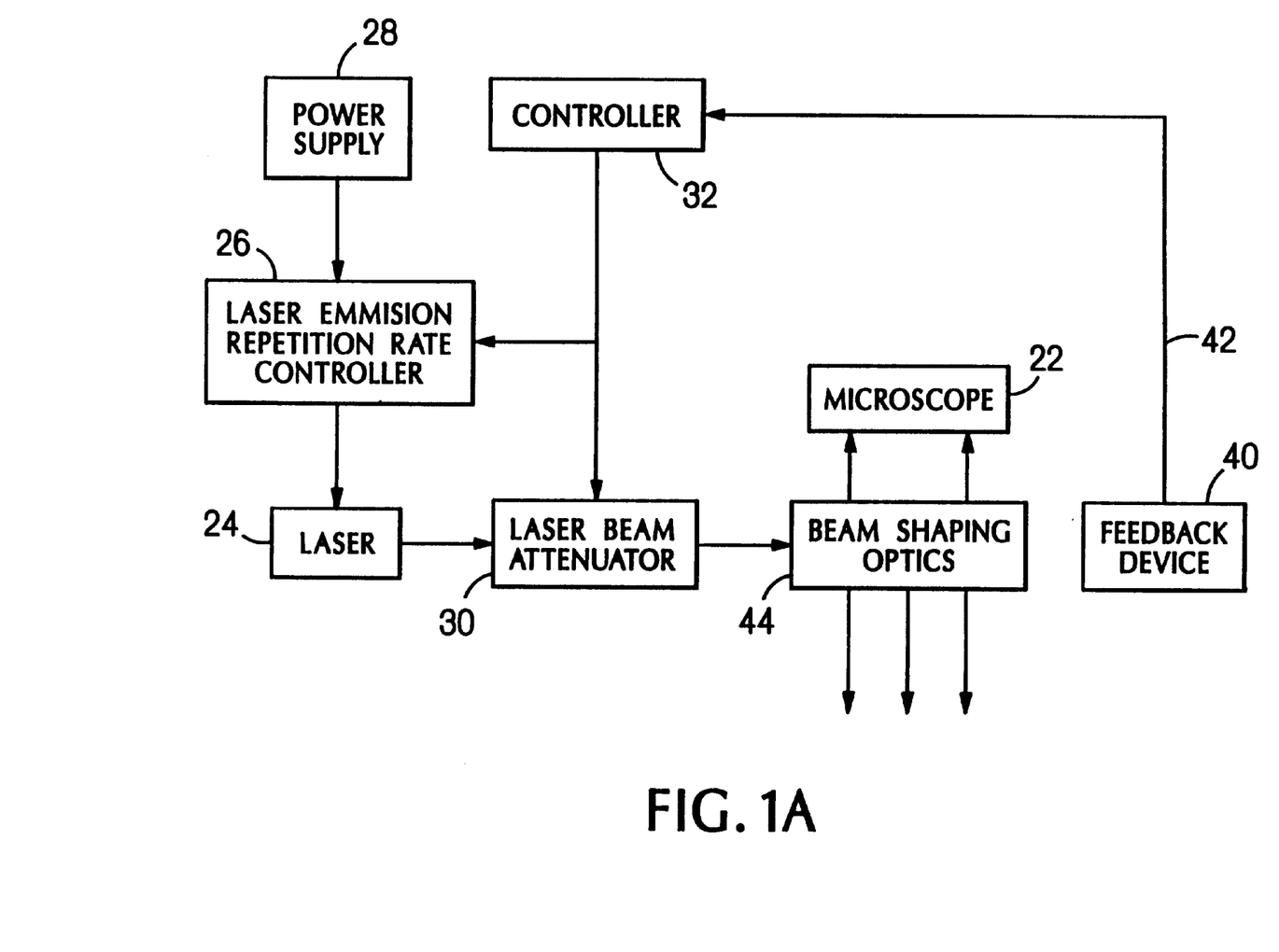
FIG. 1A is a schematic diagram illustrating the relationship between optical components inside the laser source housing and the optical support assembly shown in FIG. 1.

As shown in FIG. 1A, the laser source housing 18 includes a laser 24 (e.g., an EXCIMED™ ArF excimer laser (193 nm) available from Summit Technology, Inc. of Watertown, Mass. U.S.A.; other lasers may also be used such as HF, pulsed $CO_2$, infrared lasers at wavelengths of about 2.6–3.2 $\mu$m, Er:YSGG and Er:YAG lasers) that is controlled by a laser emission repetition rate controller 26, and powered by a power supply 28. A laser beam attenuator 30 is employed to control the fluence of the laser pulses delivered from laser 24.

A controller 32 (e.g., a commercially available microprocessor-based computer) choreographs the PRK procedure based upon the parameters of zone size (34) and Diopter correction (36) which are selected by the PRK surgeon based upon the needs of patient 10. As described in detail below, based upon the input information, controller 32 optimizes the average pulse rate and the average pulse fluence for beam pulses 38 that are delivered to the patient's cornea.

A feedback device 40, such as a profilometer or keratometer (e.g., a PHOTOKERATOSCOPE™ manufactured by Sun Contact Lens Company of Kyoto, Japan, or a CORNEASCOPE™ manufactured by International Diagnostic Instruments Limited, Broken Arrow, Okla. U.S.A.), sends signals to the controller via a feedback path 42, for precise control of the laser during the photoablation procedure.

Beam-shaping optics 44 provide a beam of a desired shape and dimension to an optical delivery system housed within optical support assembly 16. The beam-shaping optics may not always be necessary, should the laser output beam be directly usable. However, with most lasers it will normally be desirable to perform some initial shaping of the beam. For example, some types of laser systems produce beams with rectangular cross-sections (e.g., excimer lasers) and it will normally be preferable to form the beams into beams with square or circular cross-sections.

As mentioned above, it has been discovered that under certain conventional PRK conditions, detrimental phenomena may occur that can affect the accuracy and predictability of PRK procedures.

Figure 2:
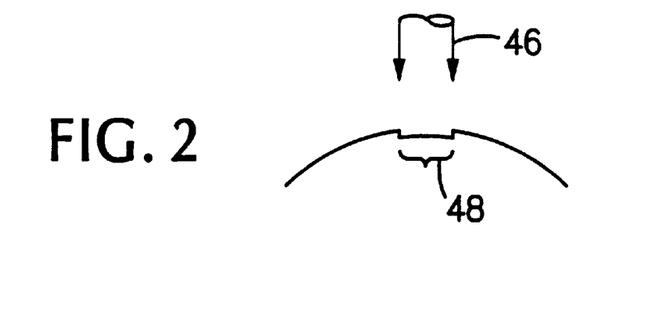
FIGS. 2–2D are elevational schematic views of a patient's cornea at successive times during a conventional PRK procedure.
Figure 2A:
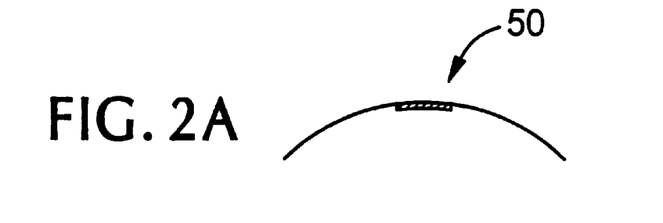
Figure 2B:
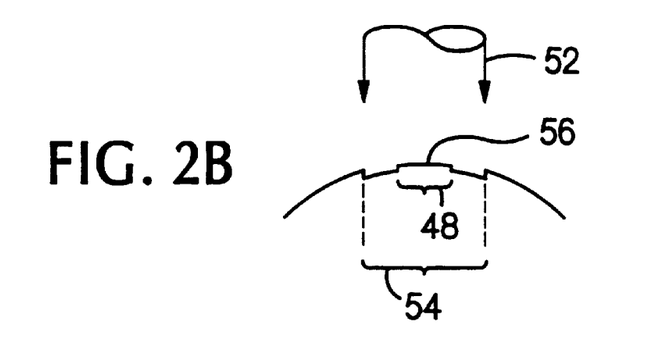
Figure 2C:
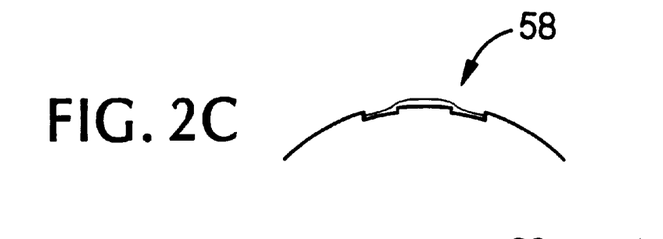
Figure 2D:
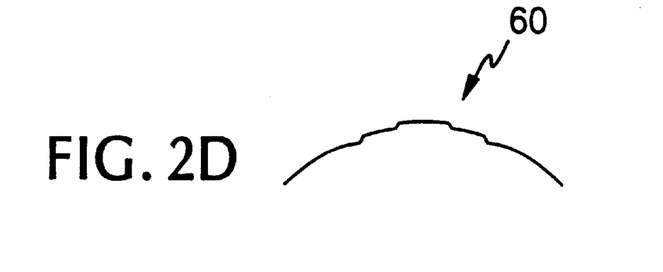

Referring to FIGS. 2–2D, under conventional PRK conditions the pulse rate and fluence levels of the photoablative beam pulses are not optimized, and the resulting accumulation of fluid in the treatment zone can detrimentally affect the outcome of the PRK procedure.

FIG. 2 shows an initial beam pulse 46 and the resulting depth of the removed corneal tissue in an ablation zone 48. As shown schematically in FIG. 2A, if the time between pulses is not short on the time-scale of corneal fluid perfusion, which has been experimentally observed to be on the order of about 1 second, ocular fluid 50 from the patient's eye can accumulate in ablation zone 48.

Referring to FIG. 2B, ocular fluid 50 can detrimentally affect the ablation uniformity of a subsequent laser beam pulse 52, which is incident upon ablation zone 54, which includes ablation zone 48, by non-uniformly altering the fluence that ultimately reaches the corneal surface as a result of the radiation absorption characteristics of the ocular fluid. Accordingly, a non-uniform corneal surface feature, in the shape of a bump 56, is created in ablation zone 54 by pulse 52. Subsequently, additional fluid 58 can accumulate in ablation zone 54, thereby causing additional non-uniform corneal surface features to be created As shown in FIG. 3D, the final corneal shape resulting from PRK under such conditions can be rough with final surface features 60 having dimensions on the order of 1–10 $\mu$m.

It is to be appreciated that the drawings presented herein are shown schematically for ease of visualization, and that in actual PRK procedures the sharp, cliff-like features shown in these drawings would not be present, and instead smooth transition regions would be present between the different ablation zones.

Assuming the corneal fluids have an absorption coefficient in the range of 3000–5000 $cm^{-1}$, for low pulse rates, enough ocular fluid could accumulate between successive beam pulses to cause attenuation in the laser beam of about 5% in the region of fluid accumulation. Non-uniform accumulation of such fluid in the treatment zone would cause a difference in the corneal tissue removal rate of 0.01–0.02 $\mu$m/pulse, relative to the removal rate expected for un-attenuated fluence levels, resulting in a cumulative error effect.

In conventional PRK practiced by Summit Technology Inc., in the past, for zone sizes of about 5 mm, beam pulse fluence levels of about 180 $mJ/cm^2$, and repetition rates of about 10 Hz, no significant non-uniformities in ablation have been observed for up to 5 Diopters of ablation. However, as the zone diameter is increased beyond about 5.5 mm (e.g., between about 6 and 10 mm) the inventors have discovered the importance of addressing the effects of fluid accumulation which if permitted to occur during PRK might cause non-uniform ablation resulting in an error in the final corneal shape which may degrade to some extent the final visual outcome. For instance, in treating a zone size of 6 mm, with 5 Diopter myopic correction, using a fluence level of about 180 mJ $cm^{-2}$, it was discovered that shifting the effective pulse rate of the laser to 20 Hz, surprisingly produced a significantly improved result in achieving the desired correction and without hazing that would be attributable to dehydration of the corneal tissue.

Following such observations, the inventors have provided a number of approaches for controlling the effects of ocular fluid accumulation in the patient's cornea in a manner substantially preventing the ocular fluid in the ablation area from affecting the photoablation of the patient's cornea during the PRK procedure, while preserving hydration of the corneal tissue.

Figure 3:
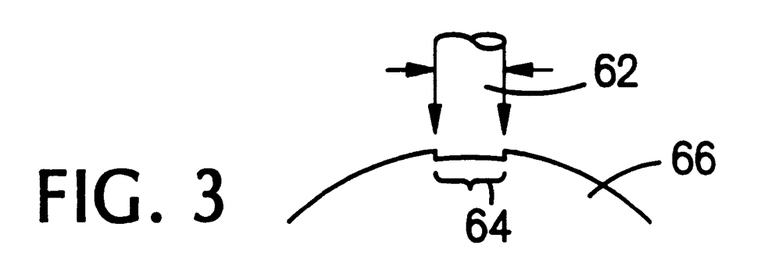
FIGS. 3–3B are elevational schematic views of a patient's cornea at successive times during a PRK procedure according to the invention.
Figure 3A:
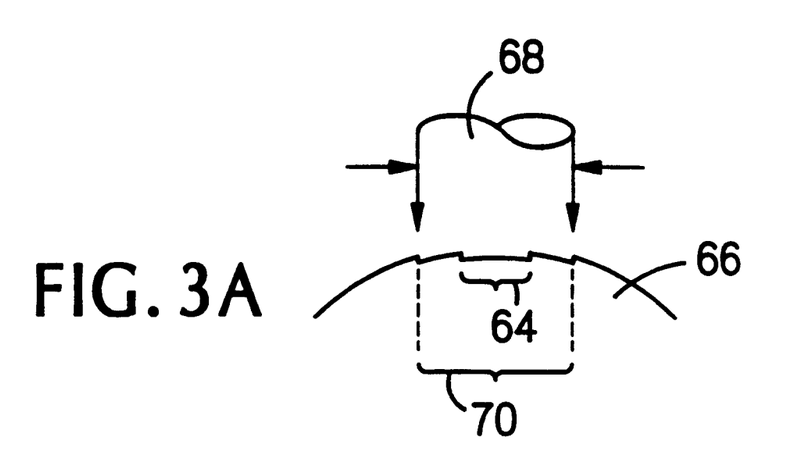
Figure 3B:
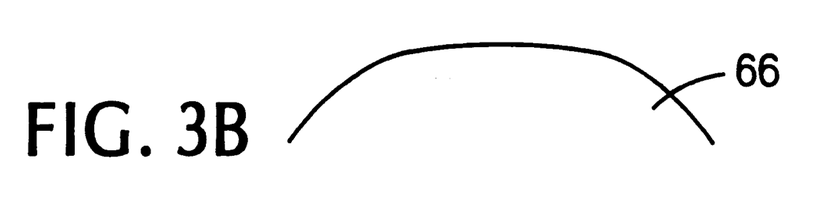

Referring to FIGS. 3–3B, according to the invention, the beam pulse rate is optimally selected, within a practical operating range, to minimize the detrimental effects of fluid accumulation in the treatment zone.

As shown in FIG. 3, an initial beam pulse 62 removes a substantially known depth of corneal tissue in an ablation zone 64 in a patient's cornea 66. Referring to FIG. 3A, a subsequent beam pulse 68 is incident upon cornea 66, in an ablation zone 70 that includes initial ablation zone 64, in a time before a substantial amount of ocular fluid could accumulate in zone 64. Thus, beam pulse 68 is capable of uniformly ablating a substantially predetermined depth into cornea 66. As shown in FIG. 3B, the shape of the corneal surface resulting from PRK performed according to the invention is substantially smooth in the treatment zone size with a diameter between about 6 and 10 mm.

Particularly for wide-area ablation procedures, the beam pulse fluence levels are preferably fixed within a fluence range of about 100 to 250 mJ cm$^{-2}$. A more preferred range under present operating conditions is 170 to 190 mJ cm$^{-2}$. In the presently most preferred embodiments, the beam fluence is about 180 mJ cm$^{-2}$. In these procedures, only the repetition pulse rate is optimally selected so that detrimental intrapulse fluid accumulation is substantially avoided. Preferably, the beam pulse repetition rate is controlled by a control switch operating at an effective average repetition rate between about 12 to 100 Hz.

As mentioned above, the effective average rate (Rep Rate, expressed in Hz) at which the beam pulses are provided to a specific site, the effective average fluence (F, expressed in mJ cm$^{-2}$) of the beam pulses, and the average diameter ($\phi$, expressed in mm) of the ablation zone, have the general relationship:

$$\text{Rep Rate} \geq C \times \phi^2 / ln(F)$$

where C is between 1.5 and 2.

In certain preferred embodiments, the fluence level of each beam pulse 62, 68 is also optimally selected, within a practical range, to minimize the above-mentioned fluid accumulation effect.

Suitable irradiation intensities (i.e., fluence value) are selected based upon the wavelength of the laser radiation and the nature of the irradiated surface. For any given wavelength of laser radiation applied to the corneal layers, there is typically a threshold value of energy density below which significant ablation does not occur. Above this threshold density, there will be a range of energy density over which increasing energy densities provide increasing depths of ablation, until a saturation point is reached, above which no significant increase in ablation rate occurs.

Typically, under conventional PRK conditions, the laser system is used to provide an ideal fluence level at the corneal surface that is slightly less than the saturation value. For example, when ablating the cornea with radiation having a wavelength of 193 nm, using wide area ablation techniques, it is preferable to provide pulses of radiation that have ideal energy densities. Typically, a single pulse with this fluence level will ablate a depth of corneal tissue in the range of about 0.1 to 0.3 μm.

However, according to the invention, for a given radiation wavelength, fluence values greater than the ideal value are used to reduce the sensitivity of each pulse to fluid that may accumulate in the ablation zone. The fluence level is preferably selected so that the amount of fluid that accumulates in the ablation zone between successive pulses absorbs an amount of beam fluence equal to the additional fluence above the ideal value. This selection is based, in part, upon a desire not to unnecessarily heat the corneal surface. According to this scheme, the additional fluence does not cause significant additional ablation in the corneal regions in which fluid has not accumulated, and instead only serves, in effect, to remove accumulated ocular fluid from the ablation zone without dehydration of the tissue.

For wide area ablation, fluence up to about 250 mJ cm$^{-2}$ may be employed In scanning systems with smaller beam size, fluence of a pulse can start as low as about 80 mJ cm$^{-2}$, but may be increased significantly with an upper limit as high as about 500 mJ cm$^{-2}$, depending on other parameters, for controlling the effect of accumulated fluid.

Because the sensitivity of the procedure varies as a power function with the Diopter value of the correction to be effected in the patient's cornea, for improved control, the system parameters can be selected to take this factor into account as well.

According to this realization, the beam pulses are selected so that, at any given site of incidence of the beam pulses in the ablation zone, the average rate (Rep Rate, expressed in Hz) at which the beam pulses are provided, the effective average fluence (F, expressed in mJ cm$^{-2}$) of the beam pulses, the average diameter ($\phi$, expressed in mm) of the ablation zone, and the dioptric power (D, expressed in Diopter) at the location of maximum correction to be effected in the patient's cornea at the location of the maximum correction, maintain the general relationship:

$$(\phi^2 \times D^2)/(ln(F) \times \text{Rep Rate}) \leq C,$$

where C is about 15.

In certain other embodiments, the excess fluid that accumulates in the ablation area is substantially evaporated during the during PRK by applying non-photoablative beam pulses to the corneal surface.

Figure 4:
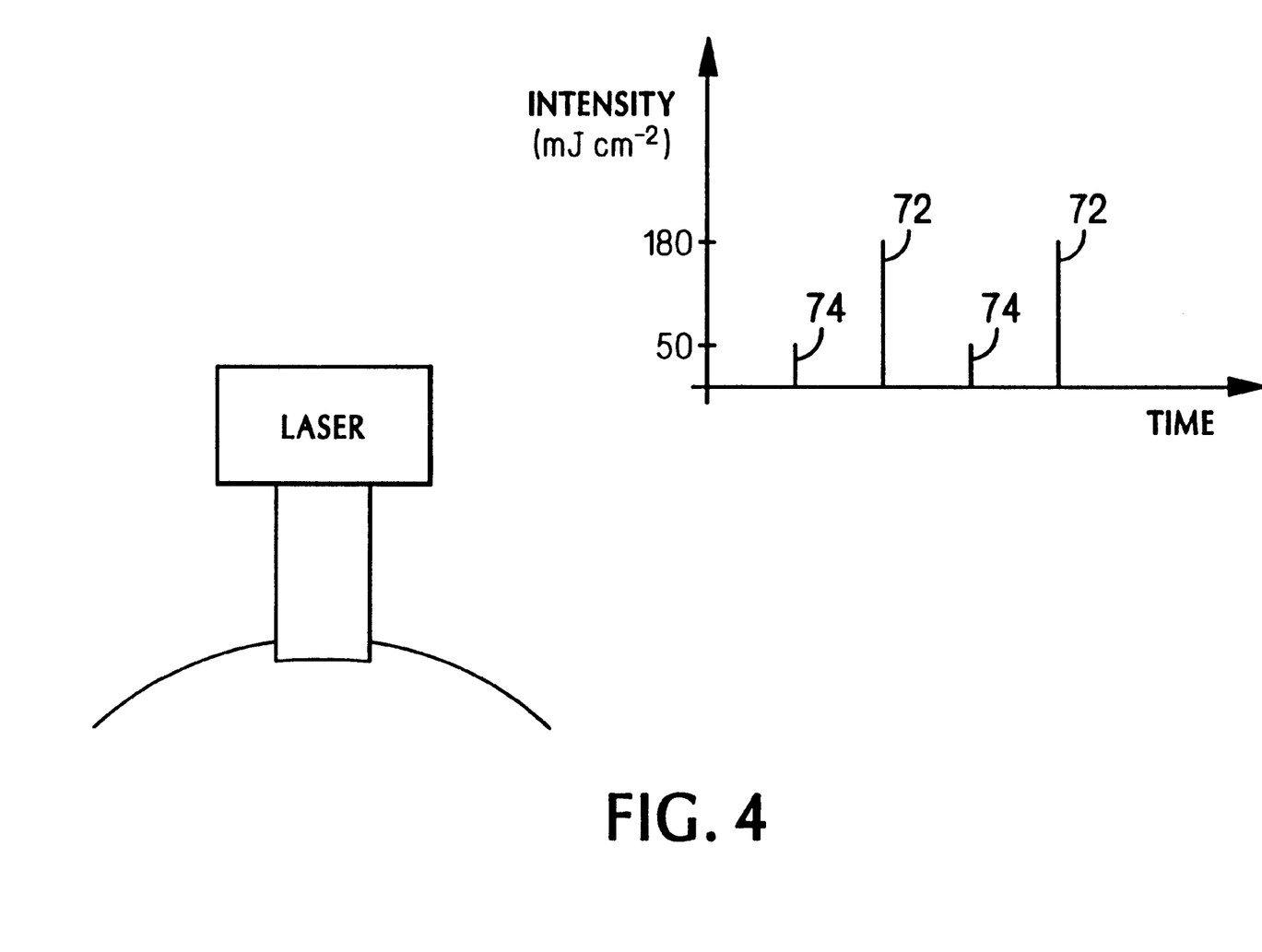
FIG. 4 is a schematic side view of a system employing precursor evaporative pulses preceding ablative pulses during PRK.
Figure 4A:
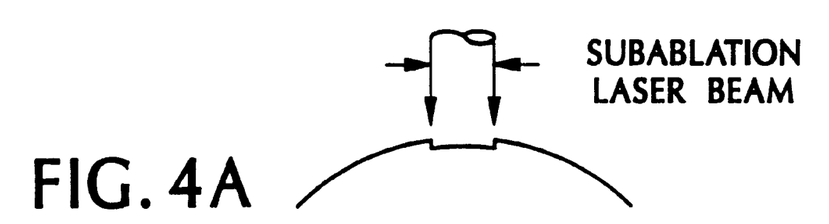
FIGS. 4A–4F illustrate steps of use of pulses of the precursor beam of subablation energy preceding ablation pulses.
Figure 4B:
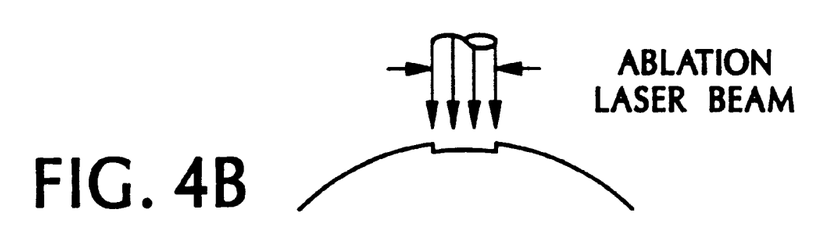
Figure 4C:
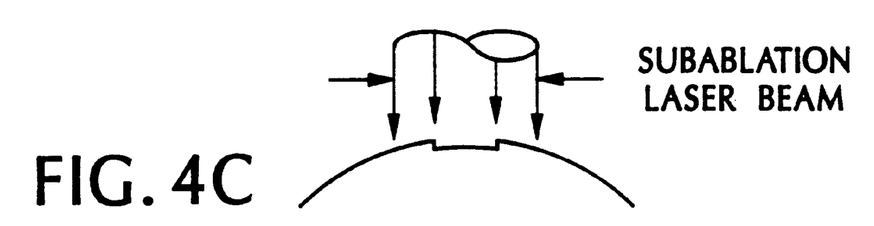
Figure 4D:
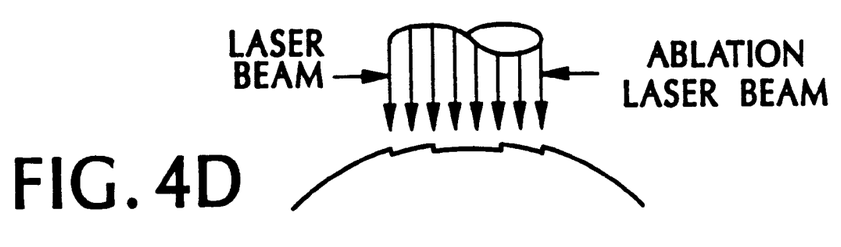
Figure 4E:
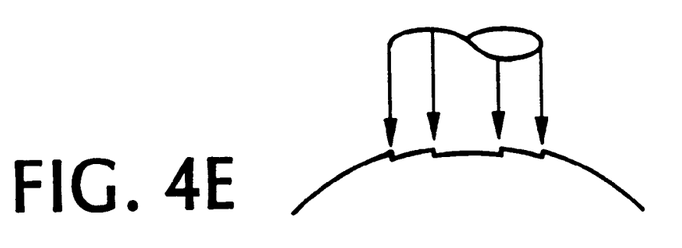
Figure 4F:
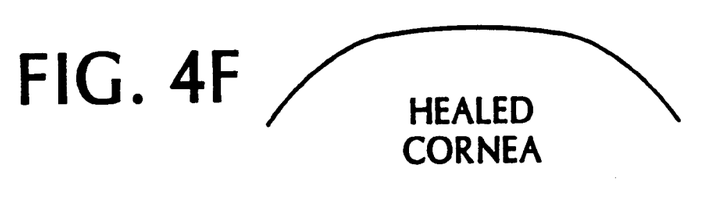
Figure 5:
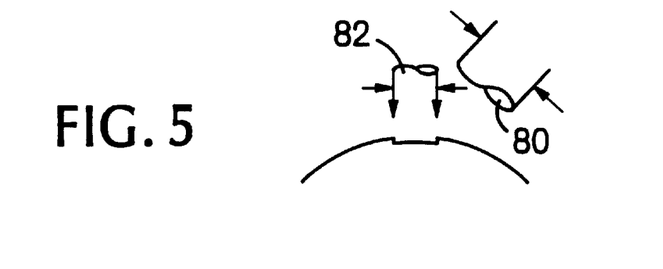
FIGS. 5–5D are elevational schematic views of a patient's cornea at successive times during a PRK procedure according to the invention in which an ocular fluid drying beam is employed.
Figure 5A:
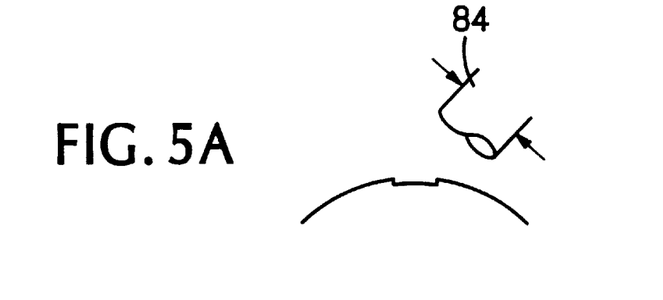
Figure 5B:
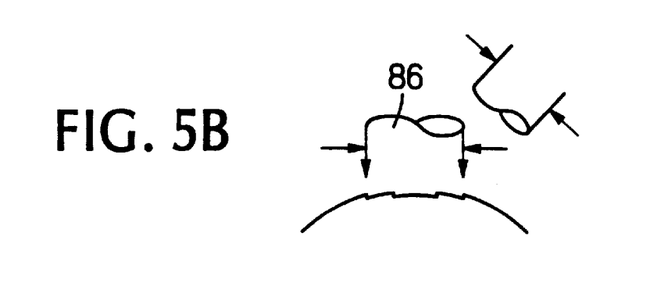
Figure 5C:
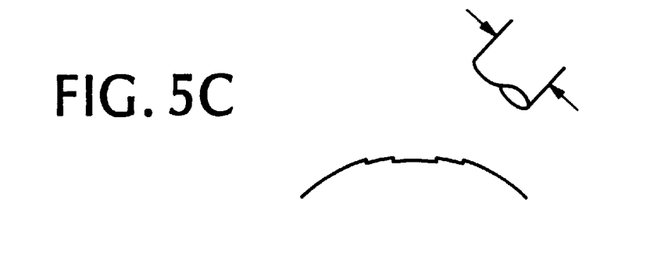
Figure 5D:
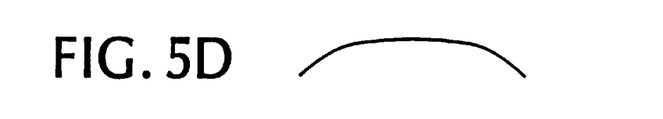

Referring to FIG. 4, in one embodiment according to this scheme, the fluence level of the actual photoablative beam pulses 72 (e.g., from an excimer laser) are preceded by precursor pulses 74 below the intensity level required for corneal photoablation. The intensity of the precursor pulses is maintained sufficiently high to substantially evaporate excess fluid that may accumulate so that the ablating pulses are substantially unaffected by accumulated ocular fluid. FIGS. 4A through 4F illustrate various stages of this procedure Alternatively, as shown in FIGS. 5–5D, pulses of infra-red radiation 80, 84 (e.g., from a pulsed $CO_2$ laser) of a wavelength selected to correspond with a peak in the wavelength-absorption profile of water can be employed to substantially evaporate the excess water accumulation in the ablation area during the PRK procedure. The amount of infrared radiation acting on a given volume at the surface, determined by wavelength, fluence, pulse duration and pulse rate, is selected to enhance evaporation of the ocular fluid. The wavelength of this radiation is selected to limit the absorption depth, for instance, to less than 100μ. For this purpose, a wavelength of about 10μ or 294μ or another wavelength corresponding to strong resonant absorption of water is selected. The infra-red beam cross-section is preferably shaped to substantially correspond to the ablation area, although in other embodiments restricting the beam to those regions tending to accumulate the most ocular fluid (central region in case of myopic correction; annular region in case of hyperopic correction) is employed. The pulses of infrared radiation 80, 84 are preferably delivered in a sequence that alternates with the incidence of the photoablative beam pulses 82, 86 on the surface of the ablation area. Alternatively, infrared pulses can be delivered to the treatment zone at twice the rate of the photoablative pulses, as shown in the drawings. As shown in FIG. 5D, the shape of the resulting surface is substantially smooth using this technique.

Figure 6:
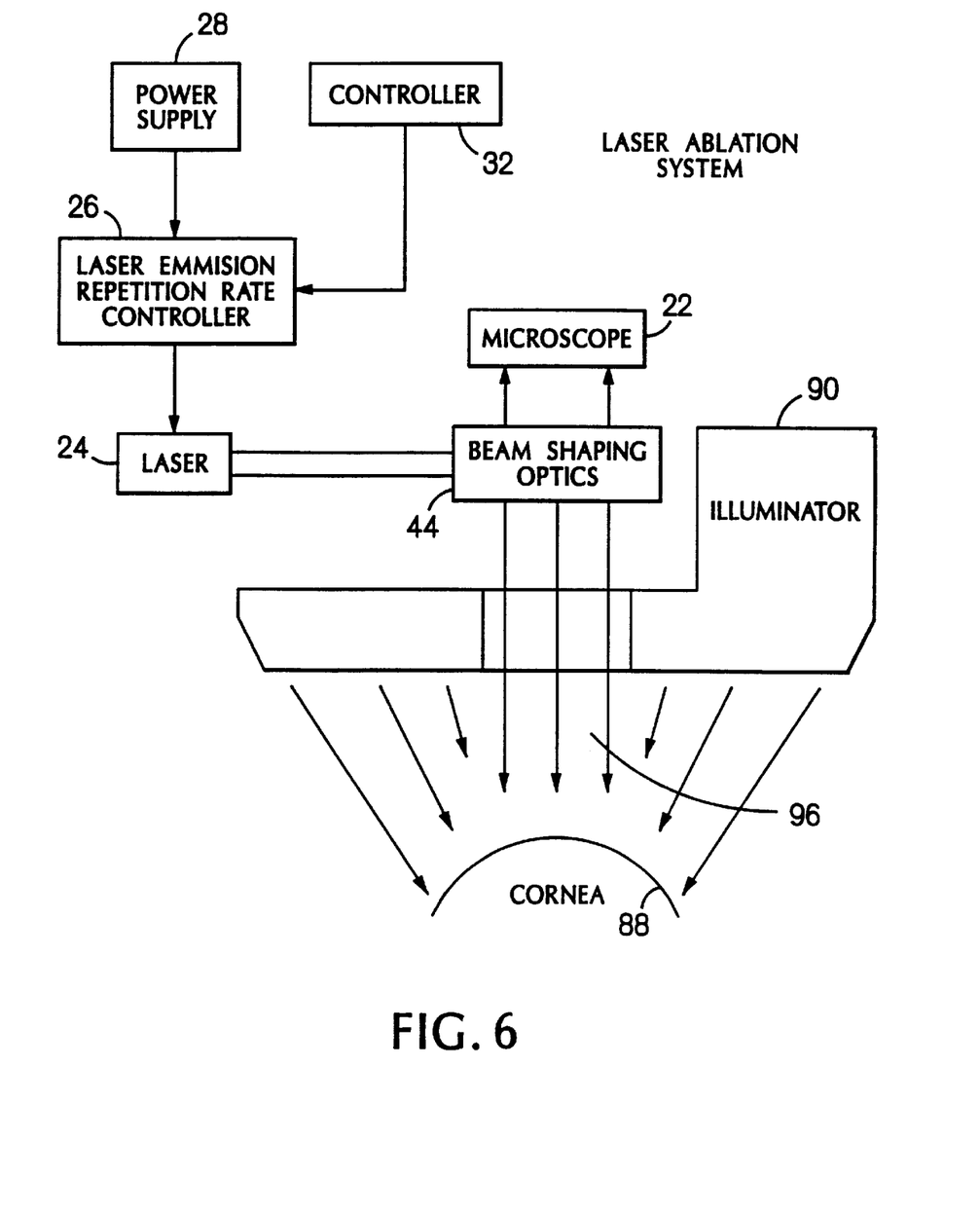
FIG. 6 is an elevational schematic view of a PRK system employing evaporative illumination for controlling accumulated fluid effects.

In an alternative embodiment, shown in FIG. 6, the effect of ocular fluid across the ablation area can be controlled by controlled application of evaporative energy to the anterior surface of a patient's cornea 88 by using a source 90 of illumination 92 having a sufficient intensity and a wavelength selected to be preferentially absorbed by the anterior 100 μm of corneal tissue. The power intensity of illumination 92 is preferably selected to be about 10 mJ cm$^{-2}$, or greater. As shown, source 90 preferably has an aperture, not shown, through which beam pulses 96 of photoablative radiation passes. Illumination 92 is preferentially delivered only to the treatment zone on the corneal surface to avoid unnecessary heating of the patient's eye.

Figure 7:
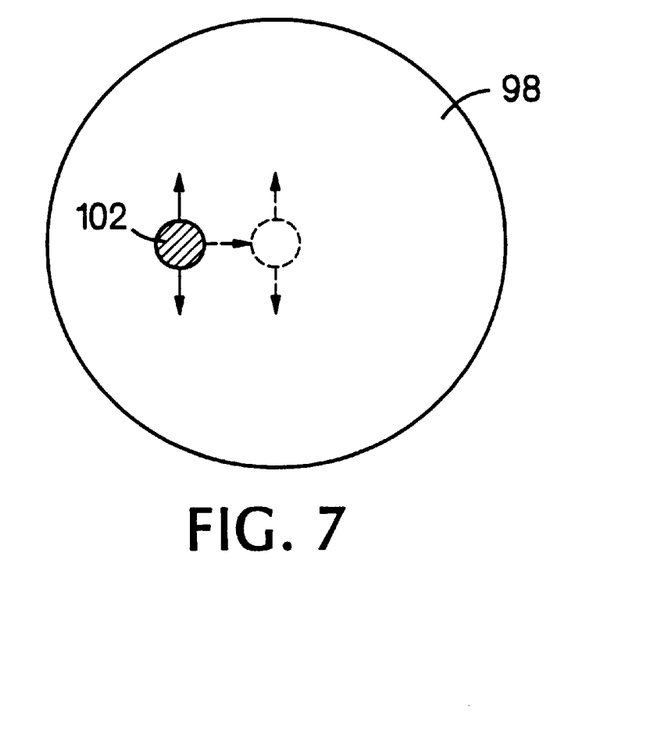
FIGS. 7 and 7A are top schematic views of a patient's cornea onto which are projected scannable beam pulses having a circular beam projection and a long, narrow beam projection, respectively.
Figure 7A:
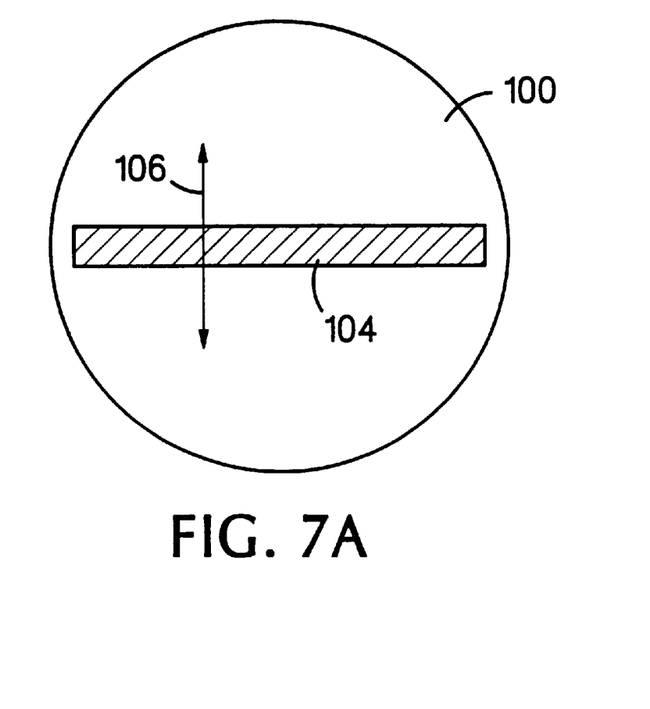

Referring to FIGS. 7 and 7A, in two embodiments according to the invention, the projection of the photoablating radiation onto corneal treatment zones 98, 100, are selected, at least in one dimension, to be substantially less than the average diameter of the respective zones.

Referring to FIG. 7, a circular projection 102 of a beam pulse is incident upon surface 98. The location of the projection of each successive beam pulse is scanned across the treatment zone, as shown in phantom, until the corneal surface is shaped in the desired manner.

Referring FIG. 7A, a long, narrow projection 104 is incident upon corneal surface 100. The long dimension of projection 104 is preferably shorter than the average diameter of treatment zone 100. Projection 104 is scanned across treatment zone 104 in the direction indicated by double-headed arrow 106, until the corneal surface is properly shaped. The intensity profile across projection 104 is preferably modified in a manner enabling the desired shaping of the treatment zone.

Using the beam projections shown in FIGS. 7 and 7A, computer algorithms, as indicated above, can be employed to particular advantage. In one instance, the regions of the deeper tissue removal can be revisited more frequently to limit the intrapulse fluid accumulation to a higher degree than that employed in more shallow regions, thus to provide a more uniform removal of the tissue during the ablative process according to the prescribed correction. Similarly, the controller can alternate the locations of the site of incidence of successive pulses so that dynamic disturbances do not affect succeeding pulses.

Figure 8:
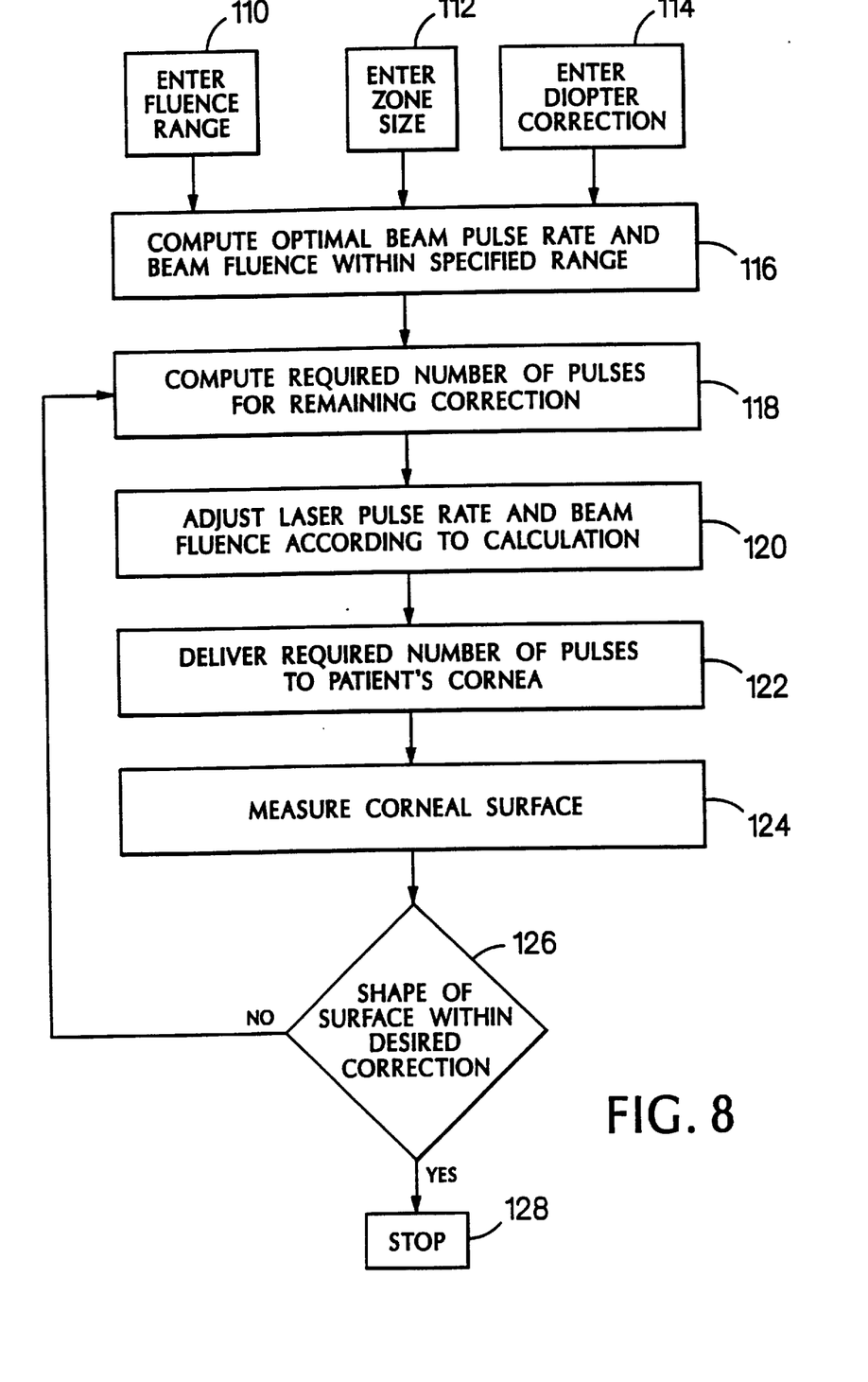
FIG. 8 is a flow diagram of a method for performing PRK according to the invention.

Referring to FIG. 8, in an exemplary method of performing PRK according to the invention, a surgeon enters into controller 32, a desired photoablative beam pulse fluence range (110), a desired treatment zone size (112), and a desired Diopter of corneal correction (114) for a given patient. A computer program running within controller 32 computes an optimal beam pulse rate and beam fluence, within the specified range (116). Controller 32 also computes the required number of pulses to achieve the desired Diopter refractive correction in the patient (118) on a conservative basis that avoids over correction. The controller outputs the computed repetition pulse rate to the laser emission repetition rate controller 26 and the computed fluence level to laser beam attenuator 30 (120). Laser source 24 then delivers the required number of pulses to the patient's cornea. Feedback device 40 measures the shape of the corneal surface and relays this information to the controller (124). If the shape is within the desired correction (126), the procedure terminates (128). However, if further correction is required, the controller recomputes the required number of pulses to achieve the desired Diopter refractive correction (118).

In certain embodiments, drugs can be topically applied to the cornea to regulate and reduce the release of corneal fluids so as to control the uniformity of corneal hydration during PRK. Preferred ocular fluid-controlling drugs include phenol-barbital and carbonic-anhydrase inhibitors such as acetazolamide which has an inhibiting effect on fluid proliferation.

It should be noted that further preferred embodiments employ selected combinations of the above-described schemes, depending upon the parameters of the system, in order to avoid non-uniform material removal problems. The combinations are selected to achieve more predictable and accurate results.

The further features described in an application entitled Improvements in Photo-Refractive Keratectomy, filed contemporaneously herewith, and assigned to Summit Technology Inc. to whom the present invention is assigned, the contents of which are hereby incorporated by reference, can also be combined with useful effect with the features taught here.

What is claimed is:

1. In a system for performing a photorefractive keratectomy procedure employing pulses of photoablative radiation to selectively ablate corneal tissue of a patient's eye in an ablation area of a given size on an anterior corneal surface to produce a desired magnitude of refractive correction in corneal tissue, the improvement comprising:
   a programmable controller that is programmed to select a repetition rate for the pulses of photoablative radiation during the photorefractive keratectomy procedure based on the magnitude of the desired refractive correction and the given size of the ablation area to reduce intrapulse fluid accumulation at the corneal surface while maintaining hydration of the corneal tissue.

2. The system of claim 1 wherein the programmable controller selects the repetition rate to be between about 12 to 100 Hz.

3. A system for performing photorefractive keratectomy to produce a desired refractive correction in a cornea of a patient's eye, the apparatus comprising
   a source of ablative radiation for providing a plurality of successive beam pulses of radiation for removing corneal tissue from the patient's eye by photoablation;
   a beam pulse delivery system, disposed between the radiation source and the patient's eye, for applying the beam pulses to the patient's cornea, over an ablation zone with a diameter in excess of 5.5 mm; and
   a programmable controller that is programmed to select an average rate that pulses are delivered to the ablation zone and to select a fluence level during photorefractive keratectomy based on the magnitude of the desired refractive correction and the diameter of the ablation zone to reduce intrapulse accumulation of ocular fluid at a plurality of sites of incidence of the beam pulses in the ablation zone.

4. The system of claim 3 wherein the programmable controller is constructed and arranged to provide the beam pulses selected so that, at any given site of incidence of the beam pulses in the ablation zone, the average rate (Rep Rate, expressed in Hz) at which the successive beam pulses are provided, an average fluence (F, expressed in mJ cm$^{-2}$) of the beam pulses, and an average diameter ($\phi$, expressed in mm) of the ablation zone, have the general relationship:

$$\text{Rep Rate} \geq C \times \phi^2 / \ln(F)$$

where C is between 1.5 and 2.

5. The system of claim 3 wherein the programmable controller is constructed and arranged to provide the beam pulses selected so that, at any given site of incidence of the beam pulses in the ablation zone, the average rate (Rep Rate, expressed in Hz) at which the beam pulses are provided, an average fluence (F, expressed in mJ cm$^{-2}$) of the beam pulses, an average diameter ($\phi$, expressed in mm) of the ablation zone, and a dioptric power (D, expressed in Diopter) of the correction to be effected in the patient's cornea, at a location of maximum correction, the following general relationship is maintained:

$$(\phi^2 \times D^2)/(\ln(F) \times \text{Rep Rate}) \leq C$$

where C is about 15.

6. The system of claim 3 wherein the source of ablative radiation comprises an excimer laser.

* * * * *

UNITED STATES PATENT AND TRADEMARK OFFICE
CERTIFICATE OF CORRECTION

PATENT NO.    : 5,993,441
DATED         : November 30, 1999
INVENTOR(S)   : David F. Muller et al.

It is certified that error appears in the above-identified patent and that said Letters Patent is hereby corrected as shown below:

<u>Column 3,</u>
Line 35, reads "between 15 and 20". should read -- between 1.5 and 2.0 --.

Signed and Sealed this

Twelfth Day of February, 2002

Attest:

JAMES E. ROGAN
Attesting Officer     Director of the United States Patent and Trademark Office